Dec. 19, 1944. C. A. HANSEN Plant Pat. 648

CRAB APPLE TREE

Filed April 8, 1942

Inventor
Carl A. Hansen.

By Knight Bros
Attorney.

Patented Dec. 19, 1944

Plant Pat. 648

UNITED STATES PATENT OFFICE

648

CRAB APPLE TREE

Carl A. Hansen, Brookings, S. Dak., assignor of one-half to Albert C. Fischer, Chicago, Ill.

Application April 8, 1942, Serial No. 438,177

1 Claim. (Cl. 47—62)

Figure 1:
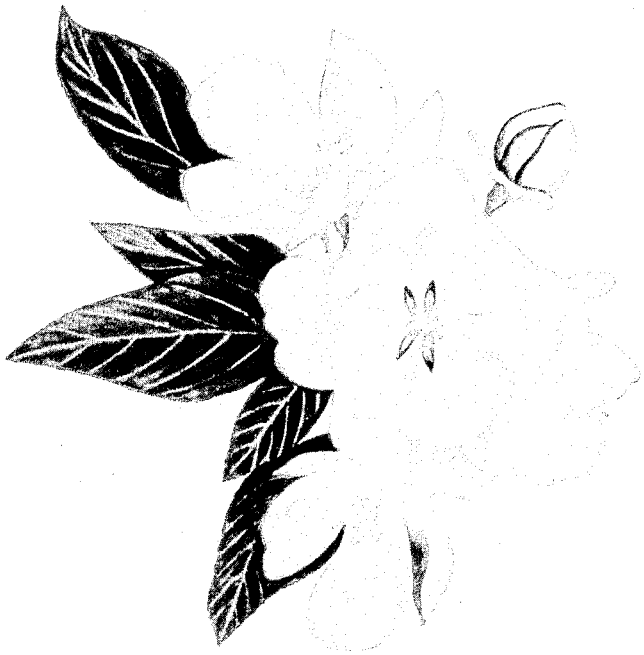
Figure 2:
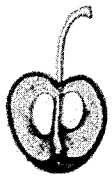

The subject of my invention is a new species of crab apple tree characterized by the production of flowers that render the tree valuable as an ornamental plant, and fruit that has a commercial value.

The tree naturally develops, by spreading into bushy form simulating the species *Malus coronaria* and in reproducing itself asexually, allows both buds and scions to develop vigorously and strongly upon other suitable stocks. Its reproductions are abnormally hardy under adverse weather or climatic conditions.

The accompanying illustration shows the blossoms of the crab apple tree and a cross sectional view of the fruit with its red meat which is borne thereby.

*Foliage.*—Its leaves approach most nearly to those of the species *Malus baccata.*

*Flowers.*—The blossoms most nearly resemble the fragrant rose-red blooms of the *Malus coronaria,* but instead of following the latter in tinging or streaking, are of a more solid color, and particularly are of deep red approximating carmine. A still more outstanding distinction resides in the fact that these blooms which approach a carmine shade, are double instead of single. The numbers of petals on the blooms vary, and as a general rule, any flower that has more than five petals is considered a double. As a rule, the flowers in accordance with the present invention have seven to nine petals. However, some of the blooms have only five petals and some have as high as fourteen petals on one flower. The blooms will vary from about one and a half (1½) inches to about two (2) inches across. Double crab blossoms and red crab blossoms have each been known, but double crab blossoms of substantially carmine shade of red were not, to my knowledge, known prior to my discovery of the plant constituting the subject matter of this specification.

*Fruit.*—The fruit is of only small crab apple size, say from one half (½) to one (1) inch in diameter, but when ripe it is juicy and edible, having a pleasant taste even in the raw state, and is particularly desirable for the red color of its meat which lends an attractive color to jelly or other preserves made from it, or from other fruits in which it may be incorporated. The fruit is produced on spurs which form on branchlets of one year of age or more, and which will, it is believed, continue fertile thereafter.

The original tree from which I have produced trees asexually was first observed by me in or about the year 1938 in my nursery in Brookings, South Dakota. It probably originated from natural cross-pollinization of a crab apple tree, such for instance as the *Malus baccata* with some flowering crab apple such as Red Silver Flowering Crab or Hopa Flowering Crab. So far as I am aware, no other tree discloses the novel identifying characteristics of the hybrid herein described.

Having thus described some of the outstanding identifying characteristics of my new crab apple tree, I declare that what is claimed as new is:

The variety of crab apple tree herein described characterized by its occasional double blossoms and its fruit having, when substantially ripe, a material content of juice, a pleasant flavor even when raw, and red meat that lends commercially desirable color to preserves made from the said fruit or from other fruit in which said fruit may be incorporated, and the extreme hardiness that enables the tree to withstand temperatures as low as 35 degrees below zero.

CARL A. HANSEN.